United States Patent [19]

Herzig et al.

[11] Patent Number: 5,468,890
[45] Date of Patent: Nov. 21, 1995

[54] IODONIUM SALTS AND PROCESS FOR THE PREPARATION THEREOF

[75] Inventors: Christian Herzig, Taching am See; Silke Scheiding, Unterschleissheim, both of Germany

[73] Assignee: Wacker-Chemie GmbH, Munich, Germany

[21] Appl. No.: 244,920

[22] PCT Filed: Dec. 17, 1992

[86] PCT No.: PCT/EP92/02932

§ 371 Date: Jun. 8, 1994

§ 102(e) Date: Jun. 8, 1994

[87] PCT Pub. No.: WO93/13110

PCT Pub. Date: Jul. 8, 1993

[30] Foreign Application Priority Data

Dec. 20, 1991 [DE] Germany ............ 41 42 327.5

[51] Int. Cl.⁶ ................ C07F 7/18; C07F 5/02; C07F 9/00

[52] U.S. Cl. ................ 556/12; 556/7; 556/13; 556/64; 556/402; 556/465; 522/15; 522/25; 568/6; 568/16; 568/17

[58] Field of Search ............ 556/12, 402, 465, 556/7, 64, 13; 568/6, 16, 17

[56] References Cited

U.S. PATENT DOCUMENTS

| | | | |
|---|---|---|---|
| 4,264,703 | 4/1981 | Crivello | 430/270 |
| 4,279,717 | 7/1981 | Eckberg et al. | 204/159.13 |
| 4,399,071 | 8/1983 | Crivello et al. | 260/440 |
| 4,513,137 | 4/1985 | Koser et al. | 546/14 |
| 4,617,238 | 10/1986 | Crivello et al. | 428/452 |
| 5,073,643 | 12/1991 | Crivello | 556/64 |

FOREIGN PATENT DOCUMENTS

| | | |
|---|---|---|
| 0334056 | 9/1989 | European Pat. Off. |
| 3935775 | 5/1991 | Germany |

OTHER PUBLICATIONS

J. Org. Chem., vol. 45, No. 8, pp. 1543–1544 (1980).
J. Org. Chem. 1981, 46, 4324–4326, "Functionalization of Alkenes and Alkynes with [Hydroxy(tosyloxy)iodo]benzene".
Derwent Abstract 91-126486/18 (1991).

*Primary Examiner*—Porfirio Nazario-Gonzalez
*Attorney, Agent, or Firm*—Martin Connaughton

[57] ABSTRACT

The invention concerns iodonium salts of the general formula $A\text{-}I^+\text{---}B\ X^-$, in which A is a group of the general formula

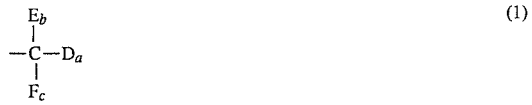
(1)

in which C is a monovalent aromatic hydrocarbon group with 6 to 14 carbon atoms or a monovalent aromatic hydrocarbon group containing at least one oxygen and/or sulphur atom and with 5 to 14 atoms in the aromatic ring, D, E and F are each substituents of C, D being a group of the formula $—(O)_x—(R)_y—SiR^1{}_3$, E being a group of the formula $—OR^2$, F being a group of the formula $—R^3$, a being 1, 2, or 3, b being 0, 1 or 2, c being 0, 1 or 2, x being 0 or 1 and y being 0 or 1, and R, R¹, R² and R³ are as defined in claim 1; B is a group of the formula

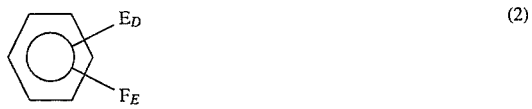
(2)

in which E and F, which are as defined above, may each be bound to the 2, 3, 4, 5 or 6 position in the benzene ring, d is 0, 1 or 2, e is 0, 1 or 2 and $X^-$ is a tosylate anion or a weakly nucleophilic or non-nucleophilic anion $Y^-$ selected from the group comprising $CF_3CO_2^-$, $BF_4^-$, $PF_4^-$, $AsF_6^-$, $SbF_6^-$, $ClO_4^-$, $HSO_4^-$ and $CF_3SO_3^-$.

6 Claims, No Drawings

IODONIUM SALTS AND PROCESS FOR THE PREPARATION THEREOF

This application is a request for U.S. examination under 35 U.S.C. 371 of International application No. PCT/EP92/02932, filed Dec. 17, 1992.

The invention relates to novel iodonium salts and a process for the preparation thereof.

Photoactive diaryliodonium salts are known from U.S. Pat. Nos. 4,264,703, 4,279,717, 4,399,071, 4,617,238 and EP-A 334 056 and are used as photoinitiators for the polymerization of cationically polymerizable organic substances, e.g. epoxides, vinyl ethers, organopolysiloxanes containing epoxy groups, organopolysiloxanes containing vinyloxy groups and olefins. However, the cationically polymerizable substances are non-polar to slightly polar, particularly if the polymerizable groups are present in organopolysiloxanes. EP-A 334 056 (laid open on Sep. 27, 1989, J. V. Crivello et al., General Electric Company) describes diaryliodonium salts where in each case an aryl radical is substituted by a long-chain alkoxy group.

It is an object of the invention to provide photoactive iodonium salts which can be used as photoinitiators for the polymerization of cationically polymerizable organic substances and which are soluble in these substances. The object is achieved by the invention.

The invention provides iodonium salts of the general formula $$A-I^+-BX^-$$

where A is a radical of the general formula

in which

C is a monovalent aromatic hydrocarbon radical having from 6 to 14 carbon atoms per radical or a monovalent aromatic hydrocarbon radical containing at least one oxygen and/or sulfur atom and having from 5 to 14 ring atoms per radical, D, E and F are each substituents of C, where D is a radical of the formula $$-(O)_x-(R)_y-SiR_3^1,$$

E is a radical of the formula $$-OR^2,$$

F is a radical of the formula $$-R^3,$$

a is 1, 2 or 3,
b is 0, 1 or 2,
c is 0, 1 or 2,
x is 0 or 1,
y is 0 or 1, preferably 1, R is a divalent hydrocarbon radical having from 1 to 18 carbon atoms per radical, which is uninterrupted or interrupted by at least one oxygen atom and/or one sulfur atom and/or one carboxyl group, $R^1$ is a monovalent hydrocarbon radical having from 1 to 18 carbon atoms per radical, which is uninterrupted or interrupted by at least one oxygen atom, $R^2$ is a monovalent hydrocarbon radical having from 1 to 18 carbon atoms per radical, which is uninterrupted or interrupted by at least one oxygen atom, and $R^3$ is a monovalent hydrocarbon radical having from 1 to 10 carbon atoms per radical, which is uninterrupted or interrupted by at least one oxygen atom and/or one sulfur atom, B is a radical of the formula

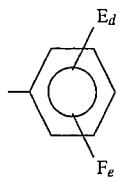

where E and F are each a radical bound to the benzene ring in the 2-, 3-, 4-, 5- or 6-position, and the radicals E and F have the meanings specified for them above, d is 0, 1 or 2,
e is 0, 1 or 2 and $X^-$ is a tosylate anion or a weakly nucleophilic or non-nucleophilic anion $Y^-$ selected from the group consisting of $CF_3CO_2^-$, $BF_4^-$, $PF_6^-$, $AsF_6^-$, $SbF_6^-$, $ClO_4^-$, $HSO_4^-$ and $CF_3SO_3^-$.

Examples of aromatic hydrocarbon radicals C are the phenyl, naphthyl and anthryl radicals.

Examples of aromatic hydrocarbon radicals C containing at least one oxygen and/or sulfur atom are the 2-furyl, 3-furyl, 2-thienyl and 3-thienyl radicals.

Preferably the radical A is a radical of the formula

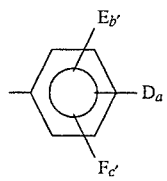

where D, E and F are each a radical bound to the benzene ring in the 2-, 3-, 4-, 5- or 6-position, D, E and F have the meanings specified for them above and b' is 0 or 1 and
c' is 0 or 1.

Examples of the divalent hydrocarbon radical R are $-CH_2-$, $-(CH_2)_2-$, $-(CH_2)_3-$, $-(CH_2)_4-$ and $-(CH_2)_6-$.

Examples of the divalent hydrocarbon radical R which is interrupted by at least one oxygen atom and/or sulfur atom and/or one carboxyl group, are $-CH_2CH_2OCH_2CH_2-$, $-CH_2CH_2-OCH_2CH_2CH_2-$ and $-CH_2CH_2OCH_2CH_2OCH_2CH_2CH_2-$.

Examples of hydrocarbon radicals $R^1$ are alkyl radicals such as the methyl, ethyl, n-propyl, iso-propyl, n-butyl, iso-butyl, tert.-butyl, n-pentyl, iso-pentyl, neo-pentyl, tert.-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical and octadecyl radicals such as the n-octadecyl radical.

Examples of hydrocarbon radicals $R^1$ interrupted by at least one oxygen atom are alkoxyalkyl radicals such as —CH$_2$CH$_2$OCH$_3$, —CH$_2$CH$_2$OCH$_2$CH$_3$ and —CH$_2$CH$_2$OCH$_2$CH$_2$CH$_3$.

Preferably, all three radicals R$^1$ bound to the Si atom together contain from 3 to 25 aliphatic carbon atoms, preferably from 10 to 20 aliphatic carbon atoms.

All the examples of radicals R$^1$ apply to the radicals R$^2$.

Examples of hydrocarbon radicals R$^3$ are alkyl radicals such as the methyl, ethyl, n-propyl, iso-propyl, n-butyl, iso-butyl, tert.-butyl, n-pentyl, iso-pentyl, neo-pentyl, tert.-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical, and decyl radicals such as the n-decyl radical; aryl radicals such as the phenyl radical.

Examples of hydrocarbon radicals R$^3$ interrupted by at least one oxygen atom and/or sulfur atom are —CH$_2$CH$_2$OCH$_3$, —CH$_2$CH$_2$OCH$_2$CH$_3$ and —CH$_2$CH$_2$SCH$_2$CH$_3$.

Examples of radicals D are
—O(CH$_2$)$_3$SiMe$_2$Et
—O(CH$_2$)$_3$SiMeBu$_2$
—O(CH$_2$)$_3$SiMeOct$_2$
—O(CH$_2$)$_3$SiBu$_3$
—O(CH$_2$)$_2$O(CH$_2$)$_3$SiMe$_2$Oct
—O(CH$_2$)$_2$O(CH$_2$)$_3$SiMeOct$_2$
—O(CH$_2$)$_2$O(CH$_2$)$_3$SiBu$_3$
—(CH$_2$)$_3$SiMeOct$_2$
—O(CH$_2$)$_3$SiEt$_3$
—(CH$_2$)$_3$SiMe$_2$Oct
(in which Me is the methyl radical, Et is the ethyl radical, Bu is the n-butyl radical and Oct is the n-octyl radical), with the radical
—O(CH$_2$)$_2$O(CH$_2$)$_3$SiMeOct$_2$
being preferred.

Examples of radicals E are the methoxy radical, ethoxy radical and n-butoxy radical.

Examples of radicals F are the methyl, ethyl, propyl, 2-methylpropyl and n-butyl radicals.

Examples of radicals A are

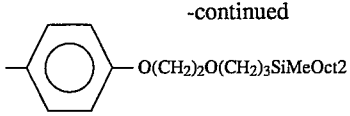

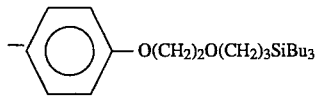

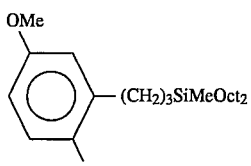

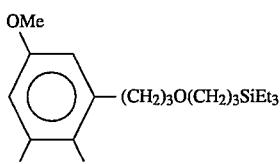

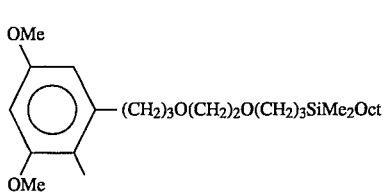

-continued

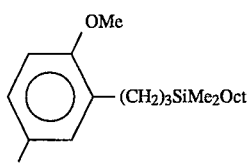

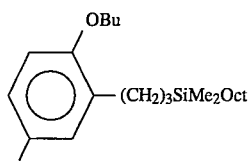

(in which Me is the methyl radical, Et is the ethyl radical, Bu is the n-butyl radical and Oct is the n-octyl radical).

Examples of radicals B are the phenyl, 4-methylphenyl, 3-methoxyphenyl and 4-methoxyphenyl radicals.

Preferred examples of anions Y$^-$ are PF$_6^-$, AsF$_6^-$ and SbF$_6^-$, particular preference being given to SbF$_6^-$.

Preferred iodonium salts are those of the formula where D and X have the meanings specified for them above.

Particular preference is given to the iodonium salt of the formula

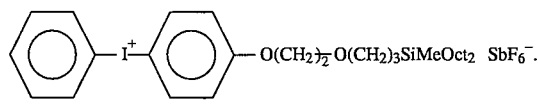

The solubility of the iodonium salts of the invention in nonpolar media, such as n-alkanes, is substantially greater than that of the comparable (same number of carbon atoms in the substituent of the phenyl radical) iodonium salts according to EP-A 334 056 mentioned in the introduction.

For example, the iodonium salt of the formula

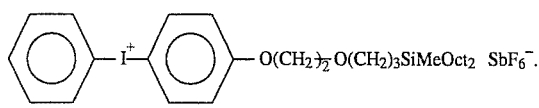

which contains 15 carbon atoms in the radical D, has unlimited solubility in cyclohexane, an iodonium salt having 20 carbon atoms in the radical D has unlimited solubility in n-heptane.

The invention further provides a process for preparing the iodonium salts, which comprises, in a 1st stage, reacting a silane of the formula $$\begin{array}{c} E_b \\ | \\ C-D_a, \\ | \\ F_c \end{array}$$

where C, D, E, F, a, b and c have the meanings specified for them above, with [hydroxy(tosyloxy)iodo]benzene, the benzene ring of which may be unsubstituted or substituted, of the formula $$\begin{array}{c} OH \\ | \\ TsO-I-B \end{array}$$

where TsO is a tosyloxy radical and B has the meaning specified for it above,
in the presence of acids and in the presence or absence of a polar solvent to give an iodonium tosylate of the formula $$A-I^+-B \ TsO^-$$

where TsO$^-$ is a tosylate anion and A is a radical of the formula $$\begin{array}{c} E_b \\ | \\ -C-D_a \\ | \\ F_c \end{array}$$

and B, C, D, E, F, a, b and c have the meanings specified for them above, and if desired, in a 2nd stage, reacting the iodonium tosylate thus obtained with an alkali metal salt of the formula $$M^+Y^-$$

where M$^+$ is an alkali metal cation and
Y$^-$ is a weakly nucleophilic or non-nucleophilic anion selected from the group consisting of
$CF_3CO_2^-$, $BF_4^-$, $PF_6^-$, $AsF_6^-$, $SbF_6^-$, $ClO_4^-$, $HSO_4^-$ and $CF_3SO_3^-$, in the presence of an organic solvent.

Examples of silanes used in the process of the invention are

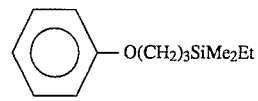

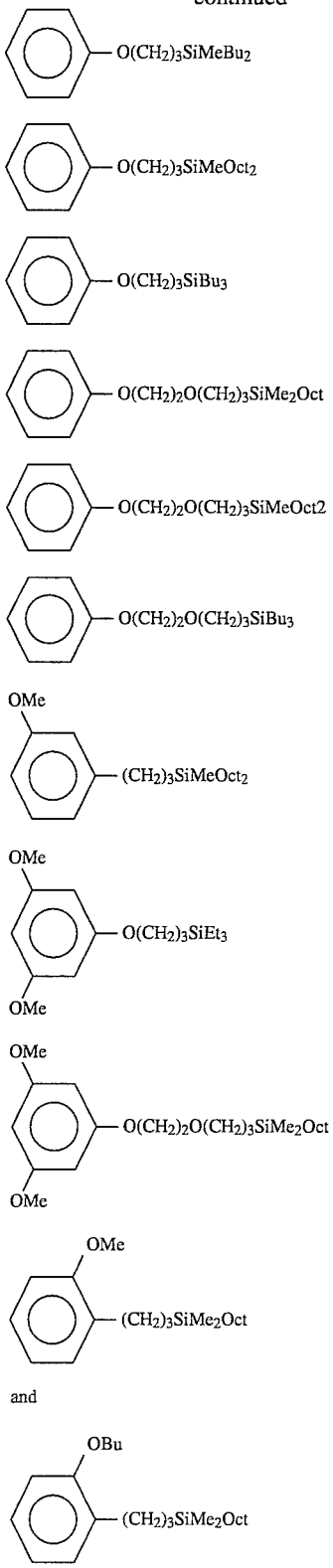

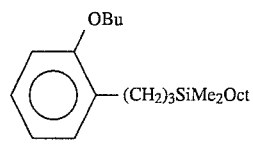

(in which Me is the methyl radical, Et is the ethyl radical, Bu is the n-butyl radical and Oct is the n-octyl radical).

The silanes are reacted with [hydroxy(tosyloxy)iodo] benzene, the benzene ring of which may be unsubstituted or substituted, ("Koser's reagent") according to the process of Neiland and Karele, Journal of Organic Chemistry, USSR 6, 889 (1970) with acid catalysis and preferably in a polar solvent at a temperature of preferably from 20° to 60° C. and preferably at the pressure of the surrounding atmosphere.

Examples of acids are carboxylic acids such as formic acid, glacial acetic acid and propionic acid, preference being given to glacial acetic acid.

Acid is preferably used in amounts of from 1 to 200 parts by weight per 100 parts by weight of silane.

Examples of polar solvents are acetonitrile, dimethylformamide, methylene chloride, 1,1,1-trichloroethane and trichloroethylene, the latter being preferred.

Polar solvent is preferably used in amounts of from 50 to 500 parts by weight per 100 parts by weight of silane.

The preparation of [hydroxy(tosyloxy)iodo]benzene is described in Neiland and Karele, Journal of Organic Chemistry, USSR 6, 889 (1970) and in Example 1 of EP-A 334 056 mentioned in the introduction.

The silanes used in the process of the invention, such as tetraalkylsilanes, can be prepared by known processes. They can, for example, be prepared as follows: phenyl allyl ether, obtainable by the method described in DE-A 39 35 775, is subjected to an addition reaction with hydrochlorosilanes in the presence of hydrosilylation catalysts such as platinum catalysts, and the phenoxyalkylchlorosilanes thus obtained are alkylated with organometallic reagents such as alkyllithium or alkyl Grignard compounds. For complete alkylation, this requires an excess (from 10 to 50 mol %) of alkyl metal reagent based on the chlorine atoms bound to Si. If not all chlorine atoms bound to Si are replaced by alkyl groups bound to Si, this leads to undesired side-reactions, such as the formation of silanols or disiloxanes, during work-up of the tetraalkylsilanes.

The longer-chain silanes which are preferably used, i.e. those having at least 15 aliphatic carbon atoms, are undistillable, mostly fluid oils. They are substantially inert chemically, but are, because of the phenyloxy group, very reactive towards electrophiles such as the iodine cation in [hydroxy(tosyloxy)iodo]benzene.

The reaction time in the 1st stage of the process of the invention is preferably from 2 to 4 hours.

[Hydroxy(tosyloxy)iodo]benzene is preferably used in at least stoichiometric amounts based on the silane used, preferably in amounts of from 1.1 to 1.4 mol per mole of silane used.

If, in the process of the invention, [hydroxy(tosyloxy)iodo]benzene is used in excess (about 20 mol %), conversions of up to 97%, in individual cases even above 97%, in each case based on the silane used, are achieved.

The iodonium tosylates obtained in the 1st stage are mostly yellow to pale orange, highly viscous liquids which dissolve very readily in most organic solvents.

The tosylate anion of the iodonium tosylates can, in a 2nd process stage, be exchanged for an anion of a strong acid.

Examples of $M^+$ are $Na^+$, $K^+$ and $Li^+$.

Preferred examples of alkali metal salts $M^+Y^-$ are $NaPF_6$, $NaAsF_6$ and $NaSbF_6$, with $NaSbF_6$ being particularly preferred.

The alkali metal salt is preferably used in amounts of from 1.1 to 1.5, preferably from 1.1 to 1.2, mol per mole of the iodonium tosylate obtained in the 1st stage of the process of the invention.

The anion exchange is preferably carried out in the presence of an organic solvent. The organic solvent used is preferably one in which the iodonium tosylate and the alkali metal salt $M^+Y^-$ dissolve well, but in which the alkali metal tosylate is sparingly soluble. Examples of organic solvents are ketones such as acetone, methyl ethyl ketone, methyl isobutyl ketone and esters such as ethyl acetate, butyl acetate and ethyl butyrate.

The reaction which may, if desired, be carried out in the 2nd stage is preferably carried out by mixing of solutions of the iodonium tosylate and the alkali metal salt $M^+Y^-$ in an organic solvent. Mixing is preferably carried out at room temperature and at the pressure of the surrounding atmosphere. However, higher or lower temperatures can also be used.

The alkali metal tosylate, such as sodium tosylate, formed in the exchange of ions precipitates after mixing and can be filtered off.

If the alkali metal salt, such as sodium hexafluoroantimonate, is used in slight excess, more than 95% of anions are exchanged. A substantially clean iodonium hexafluoroantimonate solution is obtained. Inorganic salts still present are removed by evaporation of the solution and redissolution of the oil in an organic solvent, preferably a relatively non-polar organic solvent such as toluene, cyclohexane or n-alkanes. Refiltration gives clean solutions of the iodonium salts. The organic solvent can be removed or the pure iodonium salts can, for better handling, be left in solution, preferably at a concentration of from 30 to 60%.

The process of the invention can be carried out batchwise, semi-continuously or fully continuously.

The iodonium salts are light sensitive and decompose, for example, on irradiation with ultraviolet light by a multistage mechanism which is described in the book "UV-Curing: Science & Technology" by P. Pappas on page 34. The active end product of this photolysis is viewed as the Brönsted acid formed, for example $HPF_5$, $HAsF_5$ or $HSbF_5$, which in turn initiates the polymerization of cationically polymerizable substances such as epoxides or vinyl ethers.

The iodonium salts of the invention are suitable as photoinitiators for the polymerization of cationically polymerizable organic substances such as epoxides, vinyl ethers, organopolysiloxanes containing epoxy groups, organopolysiloxanes containing alkenyloxy groups such as vinyloxy groups or propenyloxy groups, and olefins. Such substances are described, for example, in U.S. Pat. No. 5,057,549, DE-A 40 02 922 and in the patents cited in the introduction.

EXAMPLE 1 a) 4 mg of platinum in the form of hexachloroplatinic acid are added to 88.5 g (0.66 mol) of allyl phenyl ether under a nitrogen atmosphere and the mixture is heated to 80° C. 125 g of dimethylchlorosilane are metered into the mixture over a period of 2 hours, the liquid-phase temperature falling to below 50° C. The mixture is stirred for a further 6 hours under gentle reflux. Fractional distillation gives a total of 112 g of 3-phenoxypropyldimethylchlorosilane. The product has an acid number of 248 (theoretically 244).

b) 0.5 mol of an ethyl Grignard solution in diethyl ether is initially charged under a protective gas atmosphere. 92 g (0.40 mol) of the chlorosilane whose preparation is described above under a) are metered in at room temperature. The mixture is then heated to boiling and stirred for a further 2 hours at 40° C. The magnesium salts are then dissolved by addition of dilute hydrochloric acid. After phase separation, the ether phase is washed twice with 300 ml of water each time, concentrated under a light vacuum and the silane is distilled over at 3 hPa (abs.). 85 g of a colorless mobile liquid which, according to the $^1$H-NMR spectrum, is pure 3-phenoxypropyldimethylethylsilane, are obtained. The iodine number (=the number which indicates how many g of iodine are bound by 100 g of the substance)

is 115.2 ( theoretically 114.4).

c) 11.1 g (0.05 mol) of the tetraalkylsilane whose preparation is described above under b) are mixed with 10 g of acetonitrile, 3 g of glacial acetic acid and 25 g of [hydroxy-(tosyloxy)iodo]benzene and the mixture is stirred for 2 hours at 40° C., the [hydroxy(tosyloxy)iodo]benzene dissolving completely. The mixture is washed with 150 ml of water and concentrated at 30° C. and 3 hPa (abs.). The approximately 30 g of crude product are recrystallized from a mixture of 50 ml of toluene and 70 ml of n-heptane. After drying, 22.8 g of [4-( 3-dimethylethylsilylpropyloxy)phenyl]phenyliodonium tosylate having a melting point of 128° C. are obtained.

The solubility of the iodonium tosylate in toluene is examined. The results are summarized in Table 1.

d) For the anion exchange of TsO$^-$ for SbF$_6^-$, 12.0 g of the iodonium tosylate whose preparation is described above under c) are dissolved in 20 ml of acetone and a solution of 6.0 g of sodium hexafluoroantimonate in 30 ml of acetone is added with good stirring. Stirring is continued for a further hour and the precipitate of sodium tosylate is filtered off. After evaporation of the acetone at 40° C. in vacuo, the crude product is taken up in toluene and the residual sodium salts are filtered off. All solvent residues are removed in vacuo and 11.8 g of a yellowish oil are obtained as residue. After addition of cyclohexane, the oil is recrystallized and after washing with cyclohexane and drying in vacuo, a white crystalline powder having a melting point of 64°–66° C. is obtained.

The solubility of the iodonium hexafluoroantimonate in toluene is examined. The results are summarized in Table 1.

Comparative experiment 1 a) (4-Octyloxyphenyl)phenyliodonium tosylate is prepared as described in Example 1 of EP-A 334 056 mentioned in the introduction. The solubility of this iodonium tosylate in toluene is compared with that of the iodonium tosylate of Example 1 c) of the invention (the number of atoms of the two compounds being identical). The results are summarized in Table 1.

b) (4-Octyloxyphenyl)phenyliodonium hexafluoroantimonate is prepared as described in Example 1 of EP-A 334 056 mentioned in the introduction. The solubility of this iodonium hexafluoroantimonate in toluene is compared with that of the iodonium hexafluoroantimonate of Example 1 d) of the invention (the number of atoms of the two compounds being identical). The results are summarized in Table 1.

TABLE 1

| Example or Comparative Experiment | g of iodonium salt/100 g of toluene |
| --- | --- |
| E 1c) TsO$^-$ | 1.9 |
| E 1d) SbF$_6^-$ | >100 |
| C 1a) TsO$^-$ | 0.45 |
| C 1b) SbF$^-$6 | 20 |

The solubility difference between the iodonium salts of the invention and those of EP-A 334 056 is considerable. Since the iodonium salts of EP-A 334 056 are practically insoluble in n-alkanes, the solubility in toluene is given.

EXAMPLE 2 a) 690 g of 2-phenoxyethanol together with 470 g of allyl chloride are added to a solution of 600 g of sodium hydroxide and 14 g of trimethylbenzylammonium chloride in 600 ml of water. The mixture is heated under reflux and stirred vigorously until the gas space temperature has reached about 90° C. After cooling the mixture, 1.1 l of water are added and, after the salts have completely dissolved, the aqueous phase is separated off. The organic phase is then washed a further two times with 300 ml of 10% strength sodium chloride solution each time. The organic phase is fractionally distilled at 8 hPa (abs.), and 877 g (98.5% of theory) of pure 2-allyloxyethyl phenyl ether are isolated at 73°–76° C.

b) Under a nitrogen atmosphere, 8 mg of hexachloroplatinic acid are added to 178 g (1.0 mol) of 2-allyloxyethyl phenyl ether, the preparation of which is described above under a), and the mixture is heated to 70° C. 169 g (1.25 mol) of trichlorosilane are added dropwise to the mixture over a period of 2 hours and the mixture is stirred for a further 2 hours at 70° C. The crude product is purified by distillation in vacuo, giving 250 g of 3-(2 -phenoxyethoxy)propyltrichlorosilane having an acid number of 531.

c) The chlorosilane whose preparation is described above under b) is alkylated by 800 ml of a 1.7 molar n-butyl Grignard solution (36% excess) in diethyl ether being initially charged under an argon atmosphere and 105 g of the chlorosilane being added dropwise. The mixture is stirred for a further 5 hours at reflux temperature and the magnesium salts are dissolved by addition of dilute hydrochloric acid. After separating off the clear ether phase, this is washed twice with 300 ml of water each time and is concentrated in vacuo at 80° C. 122 g of 3-(2 -phenoxyethoxy)propyltributylsilane are obtained. The $^1$H-NMR spectrum shows that the silane contains, per phenoxy group, exactly 3.0 n-butyl groups directly bound to the Si atom.

d) 38 g (0.10 mol) of the tetraalkylsilane whose preparation is described above under c) are mixed with 49 g (0.125 mol) of [hydroxy(tosyloxy)iodo]benzene and 30 g of trichloroethane and 30 g of glacial acetic acid are added to the mixture. After 3 hours at 40° C., the mixture is practically clear and colored orange-yellow. The mixture is diluted with a further 150 ml of trichloroethane and washed, first with 300 ml of water, then twice with 200 ml of water each time. After separating off the aqueous phase, the iodonium salt solution is concentrated at 40° C. and 5 hPa (abs.), giving 73 g of [4-[2-(3 -tributylsilylpropyloxy)ethoxy]phenyl]phenyliodonium tosylate as an orange-red paste which, according to the $^1$H-NMR spectrum, no longer contains any starting silane.

e) 38 g (0.05 mol) of the iodonium tosylate whose preparation is described above under d) are dissolved in 80 ml of acetone and a solution of 16 g (0.06 mol) of sodium hexafluoroantimonate in 70 ml of acetone is added at room temperature. The mixture is stirred for a further hour and the precipitate of sodium tosylate is filtered off. After evaporation of the acetone at 40° C. in vacuo, the crude product is taken up in toluene and the residual sodium salts are filtered off. All solvent residues are removed in vacuo. 37 g of [4-[2-(3-tributylsilylpropyloxy)ethoxy] phenyl]phenyliodonium hexafluoroantimonate are obtained as a highy viscous oil. According to the $^1$H-NMR spectrum, the anion exchange is complete (detection limit of the tosylate: about 2 mol %).

EXAMPLE 3 a) 3 mg of platinum in the form of a divinyltetramethyldisiloxane platinum complex are dissolved in 178 g (1.0 mol) of 2-allyloxyethyl phenyl ether, the preparation of which is described in Example 2 under a), and 140 g (1.2 mol) of methyldichlorosilane are added dropwise under a nitrogen atmosphere at from 60° to 70° C. over a period of 4 hours. After a further 2 hours at the same temperature, excess chlorosilane is removed in vacuo. Fractional distillation at 9 hPa (abs.) gives, at 109°–122° C., 238 g of 3-(2-phenoxyethoxy)propylmethyldichlorosilane having an acid number of 379.

b) 149 g (0.5 mol) of the chlorosilane whose preparation is described above under a) are added dropwise under a protective gas atmosphere to a boiling n-octyl Grignard solution which had been prepared beforehand from 32 g of magnesium turnings, 215 g of 1-chlorooctane and 650 ml of tetrahydrofuran. After stirring for about 12 hours at 70° C., a mixture of 125 g of concentrated hydrochloric acid and 250 ml of water is added. The aqueous phase is separated off and the tetrahydrofuran is removed in vacuo. 222 g of 3-(2-phenoxyethoxy)propylmethyldioctylsilane having an iodine number of 56.6 are obtained as a yellow liquid. According to the $^1$H-NMR spectrum, the silane contains 2.0 n-octyl groups per phenoxy group. The acid number is less than 1 and the yield is practically quantitative.

c) 45 g (0.10 mol) of the tetraalkylsilane whose preparation is described above under b) are mixed with 49 g (0.125 mol) of [hydroxy(tosyloxy)iodo]benzene and 30 g of trichloroethane and 30 g of glacial acetic acid are added to the mixture. Slight warming occurs, after which the mixture is stirred for a further 3 hours at 40° C. After addition of 100 ml of trichloroethylene, the mixture is washed three times with 300 ml of water each time and the clear orange-yellow solution is concentrated in vacuo at 40° C. [4-[2-(3-Dioctylmethylsilylpropyloxy)ethoxy] phenyl]phenyliodonium tosylate which, according to the $^1$H-NMR spectrum, is pure and free of starting materials is obtained in almost quantitative yield as a highly viscous oil.

d) 41 g (0.05 mol) of the iodonium tosylate whose preparation is described above under d) are dissolved in 80 ml of acetone and a solution of 16 g (0.06 mol) of sodium hexafluoroantimonate in 70 ml of acetone is added at room temperature. The mixture is stirred for a further hour and the precipitate of sodium tosylate is filtered off. After evaporation of the acetone at 40° C. in vacuo, the crude product is taken up in toluene and the residual sodium salts are filtered off. All solvent residues are removed in vacuo. 43 g of [4-[2-(3-dioctylmethylsilylpropyloxy)ethoxy] phenyl]phenyliodonium hexafluoroantimonate are obtained as an orange viscous oil whose $^1$H-NMR spectrum shows the complete conversion of the tosylate.

EXAMPLE 4 a) 148 g (1.0 mol) of 2-allylanisole are mixed with 8 mg of hexachloroplatinic acid under a nitrogen atmosphere and heated to 70° C. 114 g (1.2 mol) of dimethylchlorosilane are metered into the mixture over a period of 2 hours and the mixture is stirred for a further 4 hours at 70° C. Excess dimethylchlorosilane is then removed in vacuo and 2-propenylanisole formed by isomerization is removed via a short Vigreux column. 204 g of 3-(2-anisyl)propyldimethylchlorosilane are obtained as a clear liquid having an acid number of 227.

b) For the alkylation, 122 g (0.50 mol) of the chlorosilane whose preparation is described under a) are added dropwise to 320 ml of a 1.8 molar solution of n-octylmagnesium chloride in tetrahydrofuran and the mixture is stirred for a further 6 hours at reflux temperature. To the mixture is then added sufficient dilute hydrochloric acid to form two clear phases. After separating off the magnesium salt solution, the organic phase is washed three times with 200 ml of water each time and the residual tetrahydrofuran is removed. Distillation in vacuo gives 144 g of 3-(2-anisyl)propyldimethyloctylsilane having an iodine number of 80.1 and an acid number of less than 1. The $^1$H-NMR spectrum shows a ratio of methoxy to n-octyl groups of exactly 1.0.

c) 32 g (0.10 mol) of the tetraalkylsilane whose preparation is described above under b) are mixed with 49 g (0.125 mol) of [hydroxy(tosyloxy)iodo]benzene and 20 ml of acetonitrile and 10 g of glacial acetic acid are then added to the mixture. After stirring for 3 hours at 40° C., the suspension becomes clear and 150 ml of water and 100 ml of methylene chloride are added. After washing twice with 200 ml of water each time and subsequent concentration in vacuo at 40° C., 65 g of an orange-brown oil, the $^1$H-NMR spectrum of which is in agreement with that of [3-(3-dimethyloctylsilylpropyl)-4-methoxyphenyl] phenyliodonium tosylate, are obtained.

d) 35 g (0.05 mol) of the iodonium tosylate whose preparation is described above under c) are dissolved in 80 ml of acetone and a solution of 16 g (0.06 mol) of sodium hexafluoroantimonate in 70 ml of acetone is added at room temperature. The mixture is stirred for a further hour and the precipitate of sodium tosylate is filtered off. The filtrate is washed with acetone and the solution is concentrated at 40° C. in vacuo. 200 ml of n-heptane are added and the oily phase then crystallizes through with light stirring. The practically colorless crystals are filtered off with suction, washed with n-heptane and dried. 32 g of [3-(3-dimethyloctylsilylpropyl)-4 -methoxyphenyl]phenyliodonium hexafluoroantimonate are obtained as an acicular crystalline powder having a melting point of 64.5° C. According to the $^1$H-NMR spectrum, the conversion is complete.

We claim:

1. An iodonium salt of the general formula $$A\text{-}I^+\text{-}B\ X^-$$

where A is a radical of the general formula

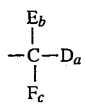

in which

C is a monovalent aromatic hydrocarbon radical having from 6 to 14 carbon atoms per radical or a monovalent aromatic hydrocarbon radical containing at least one oxygen and/or sulfur atom and having from 5 to 14 ring atoms per radical, D, E and F are each substituents of C, where D is a radical of the formula

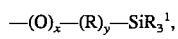

E is a radical of the formula $-OR^2$,

F is a radical of the formula $-R^3$, a is 1, 2 or 3, b is 0, 1 or 2, c is 0, 1 or 2, x is 0 or 1, y is 0 or 1, with the proviso that the sum of x+y= 1 or 2, R is a divalent aliphatic hydrocarbon radical having from 1 to 18 carbon atoms per radical, which is uninterrupted or interrupted by at least one oxygen atom and/or one sulfur atom and/or one carboxyl group, $R^1$ is a monovalent hydrocarbon radical having from 1 to 18 carbon atoms per radical, which is uninterrupted or interrupted by at least one oxygen atom, $R^2$ is a monovalent hydrocarbon radical having from 1 to 18 carbon atoms per radical, which is uninterrupted or interrupted by at least one oxygen atom, and $R^3$ is a monovalent hydrocarbon radical having from 1 to 10 carbon atoms per radical, which is uninterrupted or interrupted by at least one oxygen atom and/or one sulfur atom, B is a radical of the formula

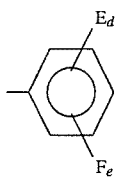

where E and F are each a radical bound to the benzene ring in the 2-, 3-, 4-, 5- or 6-position, and the radicals E and F have the meaning specified for them above, d is 0, 1 or 2, e is 0, 1 or 2 and $X^-$ is a tosylate anion or a weakly nucleophilic or non-nucleophilic anion $Y^-$ selected from the group consisting of $CF_3CO_2^-$, $BF_4^-$, $PF_6^-$, $AsF_6^-$, $SbF_6^-$, $ClO_4^-$, $HSO_4^-$ and $CF_3SO_3^-$.

2. An iodonium salt as claimed in claim 1, wherein A is a radical of the formula

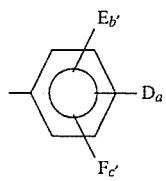

where D, E and F are each a radical bound to the benzene ring in the 2-, 3-, 4-, 5- or 6-position, D is a radical of the formula —$(O)_x$—$(R)_y$—$SiR_3^1$, E is a radical of the formula

—$OR^2$,

F is a radical of the formula

—$R^3$,

R is a divalent aliphatic hydrocarbon radical having from 1 to 18 carbon atoms per radical, which is uninterrupted or interrupted by at least one oxygen atom and/or one sulfur atom and/or one carboxyl group, $R^1$ is a monovalent hydrocarbon radical having from 1 to 18 carbon atoms per radical, which is uninterrupted or interrupted by at least one oxygen atom, $R^2$ is a monovalent hydrocarbon radical having from 1 to 18 carbon atoms per radical, which is uninterrupted or interrupted by at least one oxygen atom, $R^3$ is a monovalent hydrocarbon radical having from 1 to 10 carbon atoms per radical, which is uninterrupted or interrupted by at least one oxygen atom and/or one sulfur atom, a is 1, 2 or 3, b' is 0 or 1, c' is 0 or 1, x is 0 or 1 and y is 0 or 1, and with the proviso that the sum of x +y=1 or 2.

3. An iodonium salt as claimed in claim 1, which has the general formula

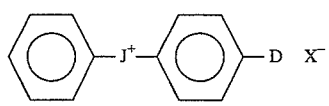

where D is a radical of the formula

—O—R—$SiR_3^1$ in which

R is a divalent hydrocarbon radical having from 1 to 18 carbon atoms per radical, which is uninterrupted or interrupted by at least one oxygen atom and/or one sulfur atom and/or one carboxyl group, $R^1$ is a monovalent hydrocarbon radical having from 1 to 18 carbon atoms per radical, which is uninterrupted or interrupted by at least one oxygen atom, and $X^-$ is a tosylate anion or a weakly nucleophilic or non-nucleophilic anion $Y^-$ selected from the group consisting of $CF_3CO_2^-$, $BF_4^-$, $PF_6^-$, $AsF_6^-$, $SbF_6^-$, $ClO_4^-$, $HSO_4^-$ and $CF_3SO_3^-$.

4. An iodonium salt as claimed in claim 3, which has the formula

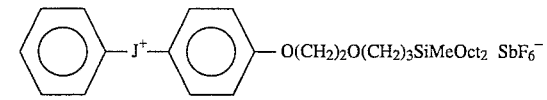

where Me is a methyl radical and Oct is an n-octyl radical.

5. A process for preparing an iodonium salt, which comprises, in a 1st stage, reacting a silane of the formula

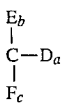

in which C is a monovalent aromatic hydrocarbon radical having from 6 to 14 carbon atoms per radical or a monovalent aromatic hydrocarbon radical containing at least one oxygen and/or sulfur atom and having from 5 to 14 ring atoms per radical, D, E and F are each substituents of C, where D is a radical of the formula —(O)$_x$—(R)$_y$—SiR$^1{}_3$, E is a radical of the formula

—OR$^2$,

F is a radical of the formula

—R$^3$, a is 1, 2 or 3,
b is 0, 1 or 2,
c is 0, 1 or 2,
x is 0 or 1,
y is 0 or 1, with the proviso that the sum of x+y=1 or 2,
R is a divalent aliphatic hydrocarbon radical having from 1 to 18 carbon atoms per radical, which is uninterrupted or interrupted by at least one oxygen atom and/or one sulfur atom and/or one carboxyl group,
R$^1$ is a monovalent hydrocarbon radical having from 1 to 18 carbon atoms per radical, which is uninterrupted or interrupted by at least one oxygen atom,
R$^2$ is a monovalent hydrocarbon radical having from 1 to 18 carbon atoms per radical, which is uninterrupted or interrupted by at least one oxygen atom, and
R$^3$ is a monovalent hydrocarbon radical having from 1 to 10 carbon atoms per radical, which is uninterrupted or interrupted by at least one, oxygen atom and/or one sulfur atom, with [hydroxy(tosyloxy)iodo]benzene, the benzene ring of which may be unsubstituted or substituted, of the formula

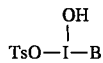

where TsO is a tosyloxy radical and
B is a radical of the formula

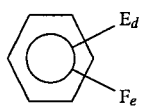

where E and F are each a radical bound to the benzene ring in the 2-, 3-, 4-, 5- or 6-position, and the radicals E and F have the meaning specified for them above,
d is 0, 1 or 2 and
e is 0, 1 or 2,
in the presence of acids and in the presence or absence of a polar solvent to give an iodonium tosylate of the formula A-J$^+$-B TsO where TsO is a tosylate anion and A is a radical of the formula

and B, C, D, E, F, a, b and c have the meaning specified for them above, and, if desired, in a 2nd stage, reacting the iodonium tosylate thus obtained with an alkali metal salt of the formula M$^+$y$^-$ where M$^+$ is an alkali metal cation and
Y$^-$ is a weakly nucleophilic or non-nucleophilic anion selected from the group consisting of CF$_3$CO$_2{}^-$, BF$_4{}^-$, PF$_6{}^-$, AsF$_6{}^-$, SbF$_6{}^-$, ClO$_4{}^-$, HSO$_4{}^-$ and CF$_3$SO$_3{}^-$, in the presence of an organic solvent.

6. The process as claimed in claim 5, wherein Y$^-$ is an anion of the formula SbF$_6{}^-$.

* * * * *